(12) United States Patent
Sato et al.

(10) Patent No.: US 9,376,415 B2
(45) Date of Patent: Jun. 28, 2016

(54) TRICYCLIC CONDENSED HETEROCYCLIC COMPOUND, PROCESS OF PRODUCING SAME, AND USE THEREOF

(75) Inventors: Seizo Sato, Hachioji (JP); Fumie Iwata, Hachioji (JP); Shoichi Yamada, Hachioji (JP); Jiro Takeo, Hachioji (JP); Akihisa Abe, Hachioji (JP); Hiroyuki Kawahara, Hachioji (JP)

(73) Assignee: NIPPON SUISAN KAISHA, LTD. (JP)

( * ) Notice: Subject to any disclaimer, the term of this patent is extended or adjusted under 35 U.S.C. 154(b) by 523 days.

(21) Appl. No.: 13/259,227

(22) PCT Filed: Mar. 24, 2010

(86) PCT No.: PCT/JP2010/055111
§ 371 (c)(1),
(2), (4) Date: Sep. 23, 2011

(87) PCT Pub. No.: WO2010/113725
PCT Pub. Date: Oct. 7, 2010

(65) Prior Publication Data
US 2012/0022153 A1 Jan. 26, 2012

(30) Foreign Application Priority Data
Mar. 30, 2009 (JP) .................................. 2009-081345

(51) Int. Cl.
C07D 307/77 (2006.01)
C12P 17/04 (2006.01)
C12R 1/465 (2006.01)

(52) U.S. Cl.
CPC .............. *C07D 307/77* (2013.01); *C12P 17/04* (2013.01); *C12R 1/465* (2013.01)

(58) Field of Classification Search
CPC ........ C07D 307/77; C12P 17/04; C12R 1/465
USPC ........................................................ 549/458
See application file for complete search history.

(56) References Cited
U.S. PATENT DOCUMENTS

2004/0014807 A1  1/2004  Vertesy et al.

FOREIGN PATENT DOCUMENTS

| AT | 256674 T | 1/2004 |
|---|---|---|
| AU | 7677600 A | 4/2001 |
| AU | 2003210205 B | 9/2003 |
| AU | 768773 B2 | 1/2004 |
| CA | 2385317 A1 | 3/2001 |
| CA | 2476618 A1 | 8/2003 |
| DE | 60007338 T2 | 11/2004 |
| DE | 10206849 A | 7/2005 |

(Continued)

OTHER PUBLICATIONS

He et al. (Chem. Eur. J. 2014, 20, 15053-15060).*

(Continued)

*Primary Examiner* — Valerie Rodriguez-Garcia
(74) *Attorney, Agent, or Firm* — Cantor Colburn LLP

(57) ABSTRACT

A compound derived from the culture product of an actinomycete and having an antitumor activity is provided. Provided is a compound represented by any one of formulas (I), (II) and (III)

or an optical isomer thereof or a pharmaceutically acceptable salt thereof

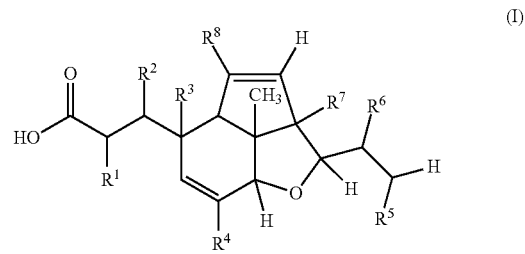
(I)

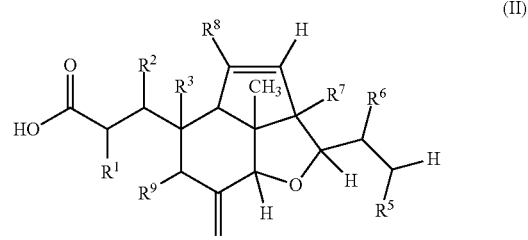

(II)

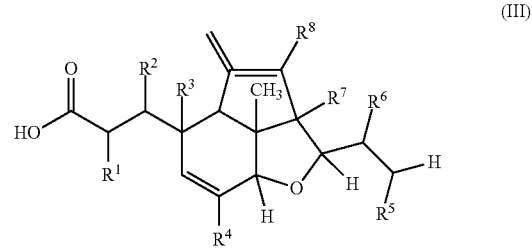

(III)

which can be isolated from the culture fluid of an actinomycete which belongs to the genus *Streptomyces*, wherein $R^1$, $R^2$, $R^5$ and $R^6$ each independently represent a hydrogen atom, a methyl group, a hydroxymethyl group, a hydroxyl group, or a double bond by which $R^1$ and $R^2$ or $R^5$ and $R^6$ are bonded; $R^3$, $R^4$, $R^7$ and $R^8$ each independently represent a methyl group or a hydroxymethyl group; and $R^9$ represents a hydrogen atom or a hydroxyl group.

3 Claims, No Drawings

(56) References Cited

FOREIGN PATENT DOCUMENTS

| DK | 1216237 T3 | 4/2004 |
| ES | 2211620 T3 | 7/2004 |
| HU | 9903226 A2 | 8/2002 |
| JP | 2003509508 A | 3/2003 |
| JP | 2005517710 A | 6/2005 |
| PT | 1216237 E | 4/2004 |
| WO | 01/21607 A2 | 3/2001 |
| WO | 03/068946 A1 | 2/2003 |
| WO | 2008/140150 A1 | 11/2008 |

OTHER PUBLICATIONS

Extended European Search Report for Application No./Patent No. 10758499.7-2101/2415768, dated Jul. 16, 2012.
Buchanan O.G. et al., "Sporolides A and B: Structurally unprecedented halogenated macrolides from the marine actinomycete Salinispora tropica", Org. Lett., 2005, vol. 7, No. 13, p. 2731-2734.
Fumie Iwata et al., "Idenshi Sodosei o Kagi to shita Kaiyo Kisho Hosenkin ga Sansei suru Shinki Seitai Kino Bunshi", Dai 51 Kai Symposium on the Chemistry of Natural Products, Symposium Papers, Sep. 1, 2009, pp. 515-520.
Hughes C.C. et al., "The marinopyrroles, antibiotics of an unprecedented structure class from a marine *Streptomyces* sp", Org. Lett., 2008, vol. 10, No. 4, p. 629-631.
International Search Report for International application No. PCT/JP2010/055111 mailing date of May 11, 2010.
Kwon H. C. et al., "Marinomycins A-D, antitumor-antibiotics of a new structure class from a marine actinomycete of the recently discovered genus "*Marinispora*"", UJ. Am. Chem. Soc., 2006, vol. 128, p. 1622-1632.
Sato S. et al., "Indoxamycins A-F. Cytotoxic tricycklic polypropionates from a marine-derived actinomycete", J. Org. Chem., Jul. 2, 2009, vol. 74, p. 5502-5509.
Sedakova L. A. et al., "Antitumor and toxic effects of amotin", Eksperimental naya Onkologiya, 1987, vol. 9, No. 5, p. 76-77.

\* cited by examiner

TRICYCLIC CONDENSED HETEROCYCLIC COMPOUND, PROCESS OF PRODUCING SAME, AND USE THEREOF

CROSS REFERENCE TO RELATED APPLICATIONS

This is a U.S. national stage of application No. PCT/JP2010/055111, filed on Mar. 24, 2010. Priority under 35 U.S.C. §119(a) and 35 U.S.C. §365(b) is claimed from Japanese Application No. 2009-081345, filed Mar. 30, 2009, the disclosure of which is also incorporated herein by reference.

TECHNICAL FIELD

The present invention relates to a novel tricyclic condensed heterocyclic compound, a process of producing the same, and use thereof. The tricyclic condensed heterocyclic compound of the present invention has an inhibitory activity on growth of cancer cells and is useful as a pharmaceutical, especially as an antitumor agent.

BACKGROUND ART

As a result of past intensive studies, many compounds having an antitumor activity have been put into practical use. Anticancer agents that are currently used in clinical practice show temporary regression and disappearance of cancer, but they also have non-selective toxicity to normal cells, causing serious adverse effects; thus, use thereof is restricted. Further, inherently resistant cancer against which an anticancer agent is not effective and acquisition of resistance to an anticancer drug which is found mainly in cases of recurrence have also been clinical problems. Under such circumstances, creation of a new antitumor agent has still been desired.

It is known that many actinomycetes are capable of producing an antibiotic. Hence, the search for a novel compound derived from an actinomycete has widely been conducted.

SUMMARY OF INVENTION

Technical Problems

The present invention is aimed at finding a novel substance derived from a natural source and providing a novel compound having an antitumor activity.

Solution to Problems

As a result of the search for a novel compound from a culture fluid of an actinomycete belonging to the genus *Streptomyces*, the present inventors found compounds having a novel framework. The present inventors determined the activity of these compounds and found that the compounds had an inhibitory activity on cell growth of tumor cells. By the above findings, the present invention was completed. Specifically, the present invention relates to (1) to (14) below.

(1) A compound represented by any one of formulas (I), (II) and (III)

[Formula 1]

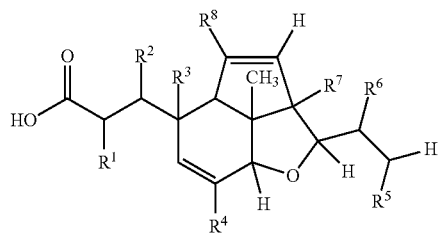

(I)

[Formula 2]

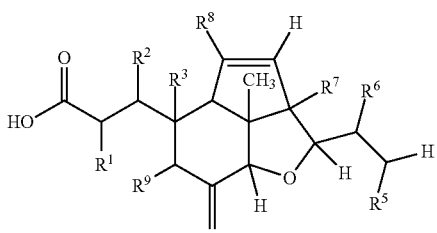

(II)

[Formula 3]

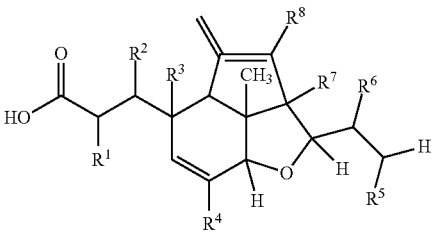

(III)

or an optical isomer thereof or a pharmaceutically acceptable salt thereof, wherein $R^1$, $R^2$, $R^5$ and $R^6$ each independently represent a hydrogen atom, a methyl group, a hydroxymethyl group, a hydroxyl group, or represent a double bond by which $R^1$ and $R^2$ or $R^5$ and $R^6$ are bonded; $R^3$, $R^4$, $R^7$ and $R^8$ each independently represent a methyl group or a hydroxymethyl group; and $R^9$ represents a hydrogen atom or a hydroxyl group.

(2) The compound of (1) represented by any one of formulas (IV), (V) and (VI)

[Formula 4]

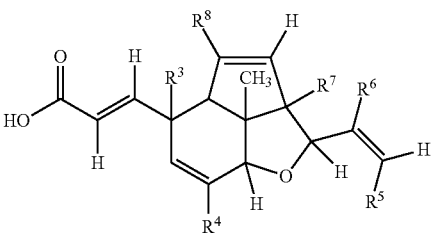

(IV)

3
-continued

[Formula 5]

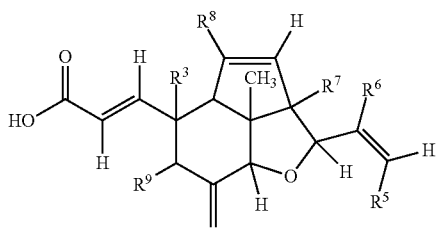

(V)

[Formula 6]

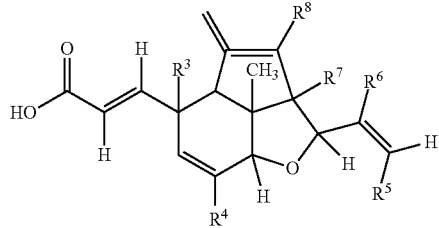

(VI)

or an optical isomer thereof or a pharmaceutically acceptable salt thereof, wherein $R^5$ and $R^6$ each independently represent a hydrogen atom, a methyl group, a hydroxymethyl group or a hydroxyl group; $R^3$, $R^4$, $R^7$ and $R^8$ each independently represent a methyl group or a hydroxymethyl group; and $R^9$ represents a hydrogen atom or a hydroxyl group.

(3) The compound of (2) represented by formula (IV) or an optical isomer thereof or a pharmaceutically acceptable salt thereof, wherein each of $R^3$, $R^4$, $R^5$, $R^6$, $R^7$ and $R^8$ is a methyl group.

(4) The compound of (2) represented by formula (IV) or an optical isomer thereof or a pharmaceutically acceptable salt thereof, wherein $R^3$ is a hydroxymethyl group, and each of $R^4$, $R^5$, $R^6$, $R^7$ and $R^8$ is a methyl group.

(5) The compound of (2) represented by formula (IV) or an optical isomer thereof or a pharmaceutically acceptable salt thereof, wherein $R^4$ is a hydroxymethyl group, and each of $R^3$, $R^5$, $R^6$, $R^7$ and $R^8$ is a methyl group.

(6) The compound of (2) represented by formula (IV) or an optical isomer thereof or a pharmaceutically acceptable salt thereof, wherein $R^5$ is a hydroxymethyl group, and each of $R^3$, $R^4$, $R^6$, $R^7$ and $R^8$ is a methyl group.

(7) The compound of (2) represented by formula (IV) or an optical isomer thereof or a pharmaceutically acceptable salt thereof, wherein $R^6$ is a hydroxymethyl group, and each of $R^3$, $R^4$, $R^5$, $R^7$ and $R^8$ is a methyl group.

(8) The compound of (2) represented by formula (V) or an optical isomer thereof or a pharmaceutically acceptable salt thereof, wherein $R^9$ is a hydroxyl group, and each of $R^3$, $R^5$, $R^6$, $R^7$ and $R^8$ is a methyl group.

(9) A pharmaceutical composition comprising as an active ingredient the compound of any one of (1) to (8) or an optical isomer thereof or a pharmaceutically acceptable salt thereof.

(10) The pharmaceutical composition of (9) which is an antitumor agent.

(11) A process of producing the compound of any one of (1) to (8), comprising: culturing a microorganism capable of producing the compound of any one of (1) to (8); and isolating the compound of any one of (1) to (8) from a product of the culturing.

(12) The process of (11), wherein the microorganism capable of producing the compound of any one of (1) to (8) is a microorganism which belongs to the genus *Streptomyces*.

(13) The process of (11), wherein the microorganism capable of producing the compound of any one of (1) to (8) is *Streptomyces* sp. NPS643 or a variant thereof.

(14) A process of producing a compound represented by formula (VII)

[Formula 7]

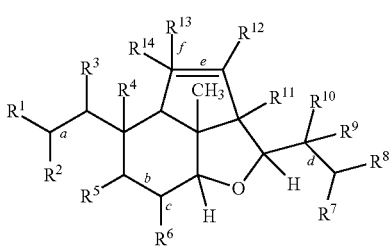

(VII)

or an optical isomer thereof or a pharmaceutically acceptable salt thereof, comprising deriving a compound represented by formula (VII) or an optical isomer thereof or a pharmaceutically acceptable salt thereof from the compound of any one of (1) to (8) or an optical isomer thereof or a pharmaceutically acceptable salt thereof used as a starting material, wherein $R^1$, $R^4$, $R^7$, $R^{10}$, $R^{11}$ and $R^{13}$ are each independently and arbitrarily selected from —$CH_2OH$, —$CH_2O$-lower alkyl, —$CH_2NH_2$, —$CH_2NH$-lower alkyl, —$CH_2N$(lower alkyl)$_2$, —$CH_2$-halogen, —COOH, —$CONH_2$ and COH; $R^2$ and $R^3$ are arbitrarily selected from combinations of (hereinafter, a halogen is referred to as "X") (X,X), (H,X), (H,OH), (OH,H) and (H,$NH_2$) (the substituents in the parentheses may be in any order) and an epoxy in which $R^2$ and $R^3$ are bonded to —O—; $R^5$ and $R^6$, $R^8$ and $R^9$, and $R^{12}$ and $R^{14}$ are each independently and arbitrarily selected from combinations of (X,X), (H,X), (H,OH), (OH,X) and (H,$NH_2$) (the substituents in the parentheses may be in any order) and an epoxy in which $R^5$ and $R^6$, $R^8$ and $R^9$, or $R^{12}$ and $R^{14}$ are bonded to —O—; and bonds indicated with a to f are each independently a single bond or a double bond.

Advantageous Effects of Invention

The compounds of the present invention are a compound having a novel framework and having an inhibitory activity on growth of cancer cells; thus, a novel anticancer agent can be provided.

DESCRIPTION OF EMBODIMENTS

As used herein, the term "halogen group" refers to a group of any one of fluorine, chlorine, bromine and iodine.

As used herein, the term "lower alkyl group" refers to, for example, a linear or branched $C_{1-6}$ alkyl group. As a $C_{1-6}$ alkyl group, for example, methyl, ethyl, n-propyl, i-propyl, n-butyl, i-butyl, tert-butyl, n-pentyl, n-hexyl or the like is used.

As a salt of the compounds of the present invention, a pharmaceutically or physiologically acceptable acid addition salt is especially preferred. Examples of such a salt that can be used include a salt of an inorganic acid (e.g., hydrochloric acid, phosphoric acid, hydrobromic acid, sulfuric acid); a salt of an organic acid (e.g., acetic acid, formic acid, propionic acid, fumaric acid, maleic acid, succinic acid, tartaric acid, lactic acid, citric acid, malic acid, oxalic acid, benzoic acid, methansulfonic acid, p-toluenesulfonic acid, benzenesulfonic acid); and a salt of an alkali (e.g., sodium, potassium, magnesium, calcium, ammonium, pyridine, triethylamine).

A process of producing a compound of the present invention will be described below.

A compound of the present invention can be obtained by culturing bacteria which are capable of producing the compound and belong to the genus *Streptomyces*, and extracting the compound from the culture fluid and purifying it by a commonly-used method. Examples of bacteria which are capable of producing the compound and belong to the genus *Streptomyces* include *Streptomyces* sp. NPS643.

*Streptomyces* sp. NPS643 is a new strain separated from the ocean. As a result of analysis of the amino acid composition of a cell wall by methods of Uchida (*Biseibutsu no kagakubunruijikkenho* (Method for the microbial chemotaxonomy and experiment), p. 5-45, Japan Scientific Societies Press, 1982) and Suzuki (*Hosenkin no bunri to dotei* (Isolation and identification of actinomycete), p. 50-55, Business Center for Academic Societies Japan, 2001), glutamic acid, glycine, alanine and LL-diaminopimelic acid were detected; thus, the type of the cell wall was inferred as Type I. The major menaquinone of the bacterial body was extracted by a method of Nishijima et al. (J. Microbiol. Methods, 28, p. 113-122, 1997), and the attribution of the quinone molecular species was determined by a method of Yamada et al. (*Biseibutsu no kagakubunruijikkenho* (Method for the microbial chemotaxonomy and experiment), p. 143-155, Japan Scientific Societies Press, 1982); the results were MK-9(H4) and MK-9(H6). As a result of homology search of 16SrDNA sequence 1386 bp of sp. NPS643 using BLAST, it was determined that the most closely related species were *Streptomyces cacaoi* subsp. *cacaoi* NBRC12748 (96.0%), *Streptomyces albus* subsp. *albus* DSM40313 (95.7%), *Streptomyces gibsonii* NBRC15415 (95.6%), *Streptomyces rangoonensis* NBRC13078 (95.6%) and *Streptomyces violaceoruber* KCTC9787 (95.6%). Further, by phylogenetic tree analysis it was determined that sp. NPS643 did not form any cluster with a known strain.

Accordingly, sp. NPS643 was determined as the genus *Streptomyces* and named *Streptomyces* sp. NPS643. It is to be noted that the deposit of the strain has been made with the International Patent Organism Depositary, the National Institute of Advanced Industrial Science and Technology, under the accession number FERM BP-11109 (date of depositary: Jun. 4, 2008).

Method of Culturing Bacteria Capable of Producing NPS643 Substance

Bacteria capable of producing NPS643 substance which belongs to actinomycete are cultured in a culture medium containing nutrients that a normal microorganism can utilize. As a nutrient source, a publicly-known nutrient source that has conventionally been used in the culture of an actinomycete can be used. For example, as a carbon source, glucose, starch syrup, dextrin, starch, molasses, animal oil, vegetable oil, etc. can be used. As a nitrogen source, soybean meal, wheat germ, corn steep liquor, cottonseed meal, meat extract, peptone, yeast extract, ammonium sulfate, sodium nitrate, urea, etc. can be used. It is effective to add, as necessary, an inorganic salt capable of producing ions of sodium, potassium, calcium, magnesium, cobalt, chlorine, phosphoric acid, sulfuric acid, etc. Further, organic and inorganic substances which promote the growth of bacteria and the production of NPS643 substance may be added as appropriate. As to a culture method, a method of culturing under aerobic conditions is suitable. A suitable temperature for the culture is 25 to 30° C.; in many cases, the culture is conducted at about 28° C. In either of shaking culture and tank culture, the accumulation of NPS643 substance produced reaches the maximum after, in general, 2 to 10 days, depending on the culture medium and culture conditions. When the amount of NPS643 substance accumulated in the culture reaches the maximum, the culture is stopped, and an intended substance is isolated from the culture fluid and purified.

Properties of sp. NPS643 tend to change easily, like other actinomycetes. For example, a mutant (spontaneous or induced), zygote or gene recombinant derived from sp. NPS643 can be used in the present invention, as long as it is capable of producing NPS643 substance.

A microorganism of *Streptomyces* other than sp. NPS643 can also be used as the bacteria capable of producing the compound of the present invention, as long as it is a microorganism capable of producing the compound of the present invention. By checking the culture fluid of the microorganism, it is possible to easily determine whether the microorganism is a microorganism capable of producing the compound of the present invention. The same applies to a microorganism other than those of the genus *Streptomyces*.

Like other actinomycetes, an actinomycete which belongs to the genus *Streptomyces* and is capable of producing the compound of the present invention can be mutated by, for example, irradiation with UV, X-rays, radiation or the like, single spore isolation, various mutation treatments or other means. Such a mutant or a spontaneous mutant is not substantially different in type from the strain described above in terms of taxonomical properties, and any of them capable of producing the compound of the present invention can be used in the process of the present invention.

To isolate the compound of the present invention from an actinomycete culture fluid, means of extraction and purification of actinomycete metabolites can be used. For example, the purification can be conducted by combining as appropriate or repeating column chromatography, ion exchange chromatography, high performance liquid chromatography, gel filtration chromatography, etc. using an organic solvent fraction, silica gel and ODS.

By using the compound of the present invention isolated from the above microorganism culture product as a material and chemically modifying the functional groups, a derivative can be synthesized using the compound of the present invention as an intermediate. Since reactive functional groups such as carboxylic acid, double bonds and hydroxyl groups are present in the compound of the present invention, the chemical modification can be conducted easily.

Examples of a method for the derivatization include publicly-known methods such as dihalogenation reaction or any equivalent reaction described in *Jikken Kagaku Koza* (Encyclopedia of Experimental Chemistry), $5^{th}$ Ed., 13, edited by The Chemical Society of Japan, p. 355-356 and 420-422, addition reaction of hydrogen halide or any equivalent reaction described in *Jikken Kagaku Koza* (Encyclopedia of Experimental Chemistry), $5^{th}$ Ed., 13, edited by The Chemical Society of Japan, p. 428-430, Brown hydroboration reaction or any equivalent reaction described in *Jikken Kagaku Koza* (Encyclopedia of Experimental Chemistry), $4^{th}$ Ed., 20, edited by The Chemical Society of Japan, p. 75-76, hydroxymercuration-demercuration reaction or any equivalent reaction described in Comprehensive Organic Synthesis (1991), Vol. 4, p. 300-305, hydroxylation reaction via halogenated hydrin or any equivalent reaction described in Journal of Organic Chemistry, (2005), Vol. 70, p. 6721-6734, Brown hydroboration amination reaction described in Journal of American Chemical Society, (1964), Vol. 86, p. 3565-3566, and synthesis reaction of epoxide or any equivalent reaction described in *Jikken Kagaku Koza* (Encyclopedia of Experimental Chemistry), 4th Ed., 20, edited by The Chemical Society of Japan, p. 213-214.

Embodiments of the present invention will be described below. However, it is understood that the scope of the present invention is not limited by the Examples.

Examples

Culture

One platinum loop of *Streptomyces* sp. NPS643 which had been grown well in a culture medium prepared by adding 1.8% artificial sea water to Humic Acid-Vitamin agar (J. Ferment. Technol., 65, 501-509 (1987)) was inoculated into a liquid culture medium containing 3% soytone and 1.8% artificial sea water and shake cultured at 28° C. at 200 rpm for 5 days. One milliliter was inoculated into 100 ml of liquid culture medium (2.5% glucose, 1.5% soytone, 0.2% yeast extract, 0.4% calcium carbonate and 1.8% artificial sea water, pH 7.2) in a 500-ml Erlenmeyer flask and cultured at 200 rpm for 6 days.

<Extraction>

Five liters of the culture fluid obtained by the above culture was divided into a supernatant and a bacterial body by centrifugal separation. The supernatant was extracted with 500 mL of ethyl acetate and 500 mL of butanol. The bacterial body was extracted with a mixed solution of methanol and ethanol and then filtered. The solvent was removed by concentration under reduced pressure to obtain a concentrate, and then the concentrate was dissolved in 200 mL of water and extracted with 200 mL of ethyl acetate and 200 mL of butanol. The organic layer was combined with the organic layer of the supernatant and then concentrated to obtain 9.75 g of residue. This residue was applied onto a column in which a chromatographic tube having a diameter of 7 cm was filled with 9 cm ODS (Fuji Silysia Chemical Ltd., DM1020T), and eluted with mixed solvents of water/methanol=3/1, 1/1, 1/3 and 0/1 to obtain 400 ml fractions. Among these fractions, the water/methanol=1/3 fraction was concentrated to obtain 401.2 mg of residue. This residue was applied onto a column in which a chromatographic tube having a diameter of 5 cm was filled with 14 cm silica gel (Kanto Chemical Co., Inc., silica gel 60N spherical, neutral, 40-50 mm), and developed with mixed solvents of chloroform/methanol=1/0, 19/1, 9/1, 3/1, 1/1 and 0/1 to obtain fractions. Among these fractions, the chloroform/methanol=9/1-3/1 fractions were concentrated to obtain 150.2 mg of residue. This residue was applied onto four TLC plates (Merck silica gel 60$F_{254}$ 20×10 cm) and developed with a mixed solvent of hexane/diethyl ether=1/2. Separation was conducted using the UV absorption as an indicator, whereby Compounds 1 to 6 were isolated in amounts of 109.0 mg, 0.5 mg, 0.5 mg, 1.0 mg, 0.5 mg and 2.0 mg, respectively.

<Identification of Compounds>

Physical properties of Compounds 1 to 6 thus isolated were as follows. The results of NMR spectra are shown in Table 1 ($^1$H NMR spectra (400 MHz, $CD_3OD$)) and Table 2 ($^{13}$C NMR spectra (100 MHz, $CD_3OD$)). From this information, structures of Compounds 1 to 6 were determined as follows.

Compound 1
(1) Color and property: Colorless oil
(2) Molecular formula: $C_{22}H_{30}O_3$
(3) High resolution mass spectrometry (Waters LTC-remier XE)
   Measured value: m/z 343.2270 ($C_{22}H_{30}O_3+H^+$)
   Theoretical value: m/z 343.2275
(4) Infrared absorption spectrum $\lambda_{max}$ (KBr) $cm^{-1}$: 3431, 2964, 2925, 2860, 1701, 1655, 1648, 1638, 1560, 1543, 1113
(5) Structural formula

[Formula 8]

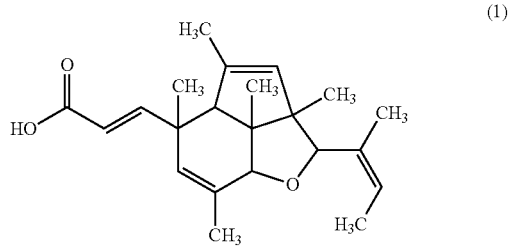

Compound 2
(1) Color and property: Colorless oil
(2) Molecular formula: $C_{22}H_{30}O_4$
(3) High resolution mass spectrometry (Waters LTC-Premier XE)
   Measured value: m/z 359.2227 ($C_{22}H_{30}O_4+H^+$)
   Theoretical value: m/z 359.2224
(4) Infrared absorption spectrum $\lambda_{max}$ (KBr) $cm^{-1}$: 3422, 2967, 2929, 2870, 1645, 1559, 1454, 1398, 1060
(5) Structural formula

[Formula 9]

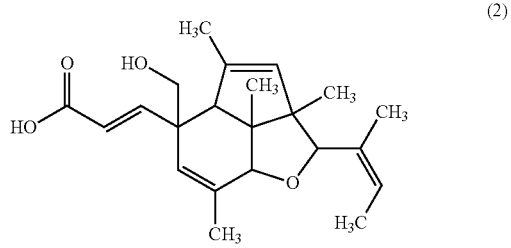

Compound 3
(1) Color and property: Colorless oil
(2) Molecular formula: $C_{22}H_{30}O_4$
(3) High resolution mass spectrometry (Waters LTC-Premier XE)
   Measured value: m/z 359.2224 ($C_{22}H_{30}O_4+H^+$)
   Theoretical value: m/z 359.2224
(4) Infrared absorption spectrum $\lambda_{max}$ (KBr) $cm^{-1}$: 3421, 2968, 2923, 2869, 1637, 1560, 1458, 1394, 1314, 1087
(5) Structural formula

[Formula 10]

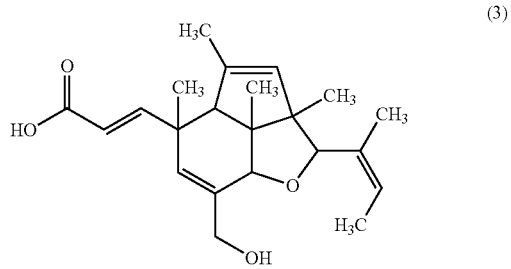

Compound 4

(1) Color and property: Colorless oil (2) Molecular formula: $C_{22}H_{30}O_4$ (3) High resolution mass spectrometry (Waters LTC-Premier XE)

Measured value: m/z 359.2224 ($C_{22}H_{30}O_4+H^+$)

Theoretical value: m/z 359.2224

(4) Infrared absorption spectrum $\lambda_{max}$ (KBr) cm$^{-1}$: 3410, 2968, 2930, 2878, 1647, 1559, 1448, 1394, 1314, 1217, 1085

(5) Structural formula

[Formula 11]

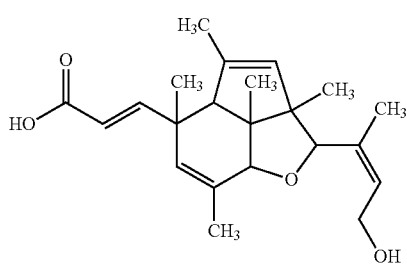

(4)

Compound 5

(1) Color and property: Colorless oil (2) Molecular formula: $C_{22}H_{30}O_4$ (3) High resolution mass spectrometry (Waters LTC-Premier XE)

Measured value: m/z 351.2084 ($C_{22}H_{29}O_3^+$)

Theoretical value: m/z 351.2038

(4) Infrared absorption spectrum $\lambda_{max}$ (KBr) cm$^{-1}$: 3420, 2965, 2929, 2869, 1637, 1569, 1457, 1396, 1314, 1191, 1097, 1042

(5) Structural formula

[Formula 12]

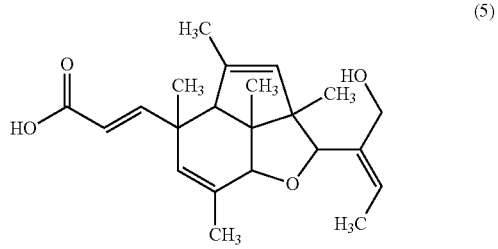

(5)

Compound 6

(1) Color and property: Colorless oil (2) Molecular formula: $C_{22}H_{30}O_4$ (3) High resolution mass spectrometry (Waters LTC-Premier XE)

Measured value: m/z 359.2223 ($C_{22}H_{30}O_4+H^+$)

Theoretical value: m/z 359.2224

(4) Infrared absorption spectrum $\lambda_{max}$ (KBr) cm$^{-1}$: 3420, 2970, 2926, 2870, 1647, 1559, 1448, 1397, 1314, 1251, 1086, 1033

(5) Structural formula

[Formula 13]

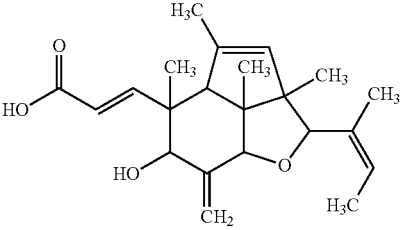

(6)

TABLE 1

| Compound 1 $\delta_H$, mult (J) | Compound 2 $\delta_H$, mult (J) | Compound 3 $\delta_H$, mult (J) | Compound 4 $\delta_H$, mult (J) | Compound 5 $\delta_H$, mult (J) | Compound 6 $\delta_H$, mult (J) |
| --- | --- | --- | --- | --- | --- |
| 4.02, s | 3.97, s | 4.11, s | 4.01, s | 4.12, s | 4.02, s |
| 5.19, s | 5.17, s | 5.19, s | 5.19, s | 5.22, s | 5.15, s |
| 2.27, s | 2.62, s | 2.27, s | 2.27, s | 2.29, s | 2.37, s |
| 5.61, s | 5.68, s | 5.68, s | 5.64, s | 5.66, s | 4.51 |
| 4.10, s | 4.07, s | 4.26, s | 4.10, s | 4.22, s | 4.14, s |
| 0.84, s | 0.82, s | 0.85, s | 0.86, s | 0.79, s | 0.82, s |
| 1.66, s | 1.69, s | 1.70, s | 1.67, s | 1.64, s | 1.65, s |
| 1.25, s | 3.37, 3.50 d (10.8) | 1.29, s | 1.23, s | 1.22, s | 1.28, s |
| 1.81, s | 1.83, s | 4.13, 4.15, s | 1.79, s | 1.80, s | 5.26, 5.06, s |
| 1.19, s | 1.19, s | 1.17, s | 1.18, s | 1.22, s | 1.18, s |
| 6.97, d (15.9) | 6.81, d (16.1) | 6.87, d (16.0) | 6.85, d (16.0) | 6.85, d (16.0) | 6.89, d (15.8) |
| 5.83, d (15.9) | 5.90, d (16.1) | 5.85, d (16.0) | 5.85, d (16.0) | 5.86, d (16.0) | 5.90, d (15.8) |
| 5.49, d (6.3) | 5.48, d (6.7) | 5.49, d (6.2) | 5.65, t (6.2) | 5.70, d (6.2) | 5.55, d (6.8) |
| 1.64, d (6.3) | 1.63, d (6.7) | 1.63, d (6.2) | 4.17, d (6.2) | 1.77, d (6.2) | 1.65, d (6.8) |
| 1.59, s | 1.57, s | 1.58, s | 1.63, s | 3.95, 4.20, d (11.9) | 1.64, s |

TABLE 2

| Compound 1 $\delta_C$, H | Compound 2 $\delta_C$, H | Compound 3 $\delta_C$, H | Compound 4 $\delta_C$, H | Compound 5 $\delta_C$, H | Compound 6 $\delta_C$, H |
|---|---|---|---|---|---|
| 92.1, CH | 91.2, CH | 90.7, CH | 90.9, CH | 83.6, CH | 90.3, CH |
| 61.2, C | 61.2, C | 59.8, C | 61.1, C | 59.7, C | 62.0, C |
| 136.9, CH | 136.4, CH | 135.3, CH | 136.9, CH | 135.2, CH | 135.4, CH |
| 139.6, C | 140.1, C | 138.3, C | 140.4, C | 138.6, C | 140.4, C |
| 65.9, CH | 58.7, CH | 65.0, CH | 65.7, CH | 64.2, CH | 66.1, CH |
| 42.3, C | 61.2, C | 40.5, C | 42.1, C | 40.6, C | 44.2, C |
| 131.5, CH | 128.1, CH | 131.0, CH | 131.6, CH | 130.1, CH | 80.3, CH |
| 136.7, C | 138.6, C | 133.9, C | 136.4, C | 137.3, C | 134.8, C |
| 85.1, CH | 84.4, CH | 80.4, CH | 85.0, CH | 87.7, CH | 85.7, CH |
| 58.1, C | 57.8, C | 56.8, C | 58.1, C | 57.4, C | 57.5, C |
| 17.7, $CH_3$ | 17.2, $CH_3$ | 17.6, $CH_3$ | 17.6, $CH_3$ | 18.7, CH3 | 17.6, $CH_3$ |
| 19.0, $CH_3$ | 19.2, $CH_3$ | 20.1, $CH_3$ | 19.2, $CH_3$ | 20.3, CH3 | 19.0, $CH_3$ |
| 30.2, $CH_3$ | 70.1, $CH_2$ | 29.4, $CH_3$ | 30.6, $CH_3$ | 29.4, CH3 | 29.1, $CH_3$ |
| 20.7, $CH_3$ | 20.7, $CH_3$ | 63.1, $CH_2$ | 20.4, $CH_3$ | 22.3, CH3 | 120.0, $CH_2$ |
| 26.6, $CH_3$ | 26.2, $CH_3$ | 25.1, $CH_3$ | 27.8, $CH_3$ | 25.5, CH3 | 28.0, $CH_3$ |
| 153.7, CH | 148.5, CH | 149.5, CH | 151.7, CH | 150.4, CH | 150.0, CH |
| 123.7, CH | 128.0, CH | 128.5, CH | 125.7, CH | 120.0, CH | 127.4, CH |
| 174.2, C | 175.7, C | 174.2, C | 175.8, C | 174.5, C | 175.8, C |
| 135.2, C | 138.6, C | 138.2, C | 136.3, C | 135.5, C | 134.8, C |
| 120.3, CH | 120.0, CH | 118.7, CH | 125.2, CH | 123.3, CH | 125.2, CH |
| 12.9, $CH_3$ | 12.9, $CH_3$ | 12.9, $CH_3$ | 59.1, $CH_2$ | 15.9, CH3 | 12.9, $CH_3$ |
| 14.4, $CH_3$ | 14.3, $CH_3$ | 15.7, $CH_3$ | 14.7, $CH_3$ | 56.7, CH2 | 14.2, $CH_3$ |

<Pharmacological Activity>

The cell growth inhibitory activity of Compound 1 was evaluated using 4 types of cancer cells. The cancer cells used were human cancer cells (HT-29, A431, NCI-H460, H-937). Compound 1 was dissolved in DMSO. One hundred milliliters of a suspension of cancer cells was charged in each 96 well micro plate (1.0 to 3.0×10³ cells/well). After 24 hours, each of solutions of Compounds 1 to 6 was added in an amount of 2 ml to 100 ml of culture fluid to give final concentrations of 3 mM, 1 mM, 0.3 mM, 0.1 mM and 0.03 mM and cultured for 72 hours. Thereafter, 20 ml of an Almar Blue reagent was added to each solution, followed by culturing for 6 hours. The growth inhibitory activity was measured by determining the fluorescence intensity with a multimicroplate reader (GENios plus microplate reader, Tecan) at a fluorescence wavelength of 590 nm and an excitation wavelength of 530 nm and calculating the $IC_{50}$ value for each cell by nonlinear regression analysis. The $IC_{50}$ value of cell growth inhibitory activity of Compound 1 is shown below.

TABLE 3

| Cancer cell | HT-29 | NCI-H460 | U937 | PC-3 |
|---|---|---|---|---|
| $IC_{50}(\mu M)$ | 0.59 | 0.58 | 1.10 | 0.82 |

The cell growth inhibitory activity of Compound 6 was evaluated using cancer cells (HT-29). The method for the evaluation was the same as the method by which Compound 1 was evaluated. The $IC_{50}$ value of cell growth inhibitory activity of Compound 6 was 0.31 µM.

INDUSTRIAL APPLICABILITY

The compounds of the present invention can provide a novel antitumor agent having an antitumor activity.

| | | |
|---|---|---|
| 0-1 | Form PCT/RO/134 (SAFE) | |
| 0-1-1 | The indications relating to deposited microorganism or other biological material (PCT Rule 13 bis) were made by: | JPO-PAS i171 |
| 0-2 | International application number | |
| 0-3 | Applicant's or agent's file reference | PCT2010-02 |
| 1 | The indications made below relate to the deposited microorganism or other biological material referred to in the description on: | 0014 |
| 1-1 | Paragraph number | |
| 1-3 | Identification of deposit | |
| 1-3-1 | Name of depositary institution | International Patent Organism Depositary (IPOD), National Institute of Advanced Industrial Science and Technology (AIST) |
| 1-3-2 | Address of depositary institution | Tsukuba Central 6, 1-1, Higashi 1-chome, Tsukuba-shi, Ibaraki 305-8566 Japan |
| 1-3-3 | Date of deposit | Jun. 4, 2008 |
| 1-3-4 | Accession number | IPOD FERM BP-11109 |
| 1-5 | Designated states for which indications are made | All designations |
| | For receiving Office use only | |
| 0-4 | This sheet was received with the international application (Yes/No) | |
| 0-4-1 | Authorized officer | |

-continued

| For International Bureau use only | |
|---|---|
| 0-5 | This sheet was received by the International Bureau on: |
| 0-5-1 | Authorized officer |

The invention claimed is:

1. A process for producing a compound of formula (I), (II) or (III)

[Formula 1]

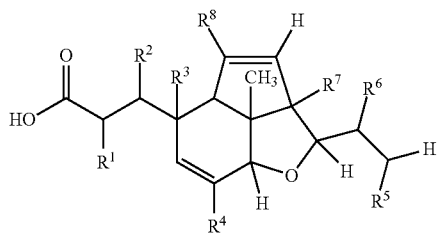

(I)

[Formula 2]

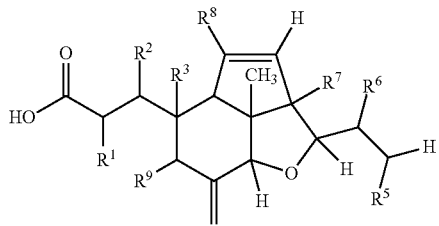

(II)

[Formula 3]

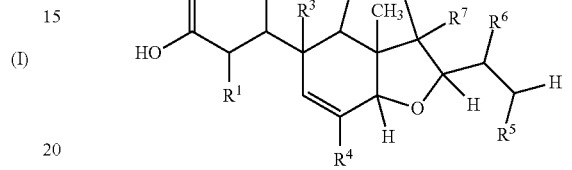

(III)

or an optical isomer thereof or a pharmaceutically acceptable salt thereof, wherein $R^1$, $R^2$, $R^5$ and $R^6$ each independently represent a hydrogen atom, a methyl group, a hydroxymethyl group, a hydroxyl group, or represent a double bond by which $R^1$ and $R^2$ or $R^5$ and $R^6$ are bonded; $R^3$, $R^4$, $R^7$ and $R^8$ each independently represent a methyl group or a hydroxymethyl group; and $R^9$ represents a hydrogen atom or a hydroxyl, the process comprising culturing a microorganism capable of producing the compound of formula (I), (II) or (III); and isolating the compound of formula (I), (II) or (III) from a product of the culturing, wherein the microorganism is cultured in a culture medium comprising about 2.5 weight percent glucose.

2. The process of claim 1, wherein the microorganism capable of producing the compound of formula (I), (II) or (III) is a microorganism which belongs to the genus *Streptomyces*.

3. The process of claim 1, wherein the microorganism capable of producing the compound of formula (I), (II) or (III) is *Streptomyces* sp. NPS643 or a variant thereof.

* * * * *